United States Patent [19]

Chen et al.

[11] Patent Number: 4,988,630

[45] Date of Patent: Jan. 29, 1991

[54] MULTIPLE BEAM LASER INSTRUMENT FOR MEASURING AGGLUTINATION REACTIONS

[75] Inventors: Fang-Chung Chen, Pine Brook; Michael L. Franklin, Parsippany, both of N.J.

[73] Assignee: Hoffmann-La Roche Inc., Nutley, N.J.

[21] Appl. No.: 42,764

[22] Filed: Apr. 27, 1987

[51] Int. Cl.$^5$ .......................................... G01N 33/546
[52] U.S. Cl. ..................... 436/533; 435/7.1; 435/808; 436/534; 436/164; 436/807; 422/73
[58] Field of Search ............... 350/394; 356/341, 343, 356/369; 435/808, 7; 436/533, 534, 164, 805, 807; 422/73

[56] References Cited

U.S. PATENT DOCUMENTS

| | | |
|---|---|---|
| 2,970,216 | 6/1961 | Magrath . |
| 3,230,475 | 1/1966 | Koester et al. . |
| 3,617,222 | 11/1971 | Matte . |
| 3,820,897 | 6/1974 | Roess ............................. 356/343 X |
| 3,990,851 | 11/1976 | Gross et al. . |
| 4,144,452 | 3/1979 | Harte . |
| 4,146,799 | 3/1979 | Pitt et al. . |
| 4,174,952 | 11/1979 | Cannell et al. . |
| 4,241,998 | 12/1980 | Farkas et al. . |
| 4,305,665 | 12/1981 | Achter et al. . |
| 4,363,551 | 12/1982 | Achter et al. . |
| 4,401,387 | 8/1983 | Takinage et al. . |
| 4,432,642 | 2/1984 | Tolles . |
| 4,443,104 | 4/1984 | Ringhardtz . |
| 4,446,239 | 5/1984 | Tsuji et al. . |
| 4,447,396 | 5/1984 | Kano .................... 422/73 |
| 4,454,233 | 6/1984 | Wang .................... 436/525 |
| 4,581,337 | 4/1986 | Frey et al. . |
| 4,708,481 | 11/1987 | Mori et al. ........................ 356/358 |
| 4,718,762 | 1/1988 | Wiget et al. . |
| 4,762,413 | 8/1988 | Namba et al. ................ 436/164 X |
| 4,766,083 | 8/1988 | Miyashita et al. ................. 436/517 |

OTHER PUBLICATIONS

Electro-Optical Systems Design, Aug. 1970, pp. 1-7.
Finley, P., Laboratory Management 9/82, pp. 34-45.
Franklin, M., "Instrumentation in Clinical Chem.", Clin. Biochem. Contemporary Theories and Technology, vol. 3, pp. 153-169 (1984).
Gross J., Nephelometry; Principals and Methods, pp. 11-14.
Litchfield, et al, Clin. Chem. vol. 30, No. 9, pp. 1489-1493 (1984).
Toyo Soda, Advertizement "Low Angle Laser Light Scattering Photometer LS-8000".
Berdnik et al, Derwent A9548K/03 (1983).
Brochure-Groupamatic-Automatic Blood Grouping System.
Salmon et al., Revue Francaise de Transfusion et d'Immuno-hematologie, Tome XXI, No. 2 (1978) pp. 279-293.
G 2000 Technical Manual (Oct. 1982).

*Primary Examiner*—Esther L. Kepplinger
*Assistant Examiner*—Carol A. Spiegel
*Attorney, Agent, or Firm*—George M. Gould; Bernard S. Leon; George W. Johnston

[57] ABSTRACT

There is described a unique instrument system employing a laser, having a polarized and collimated beam of radiation, which is split into a multitude of primary and secondary beams containing the same desirable properties of high collimation and monochromaticity. The secondary beams are used to measure simultaneously multiple antigen-antibody (Ag-Ab) agglutinations reactions involving latex particles.

2 Claims, 4 Drawing Sheets

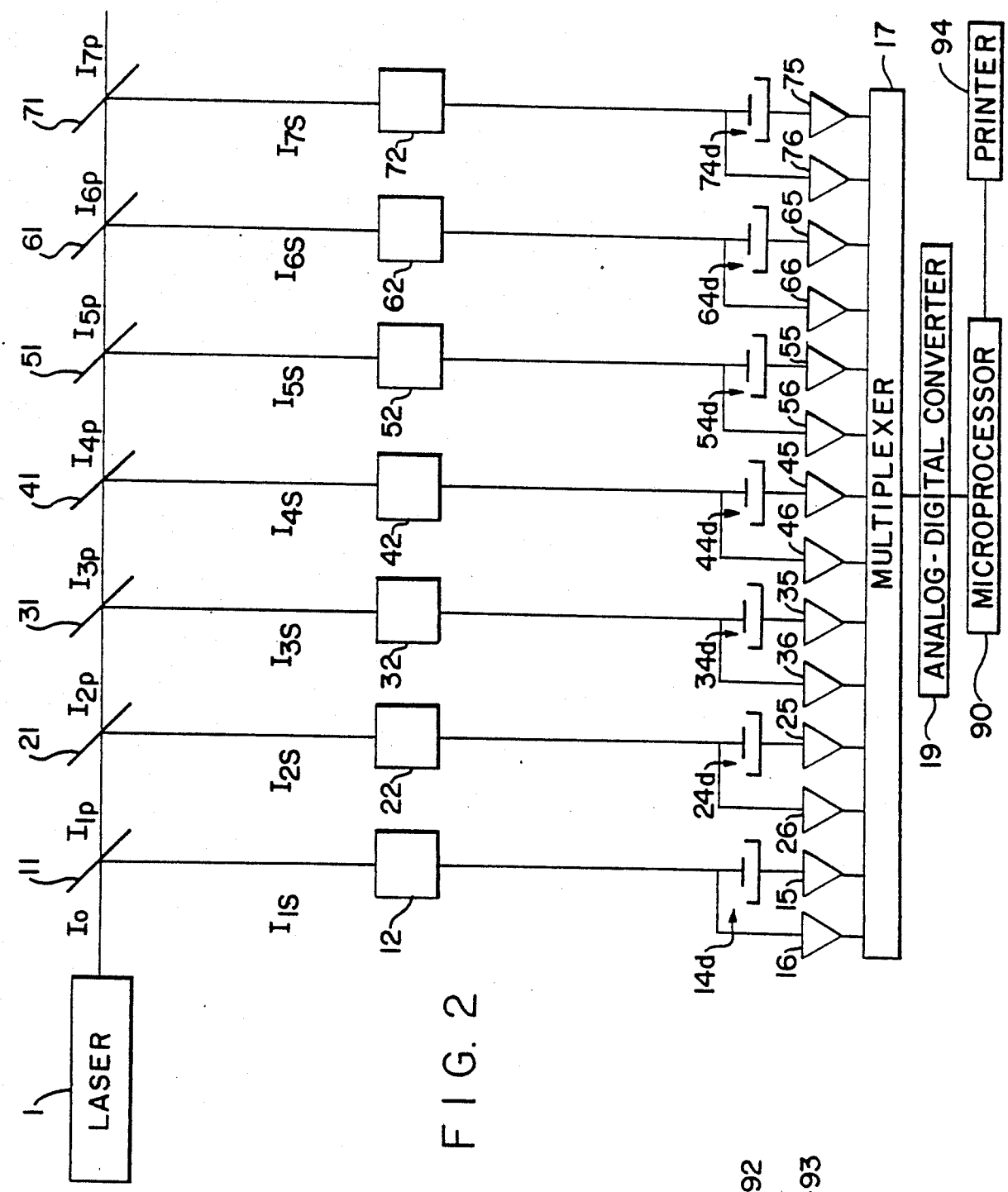

MULTIPLE BEAM LASER INSTRUMENT FOR MEASURING AGGLUTINATION REACTIONS

BACKGROUND

1. Field of the Invention

A light-scattering instrumentation system is described which allows the quantitation of latex agglutination reactions which employ immunochemistry. More particularly, the instrumentation system finds use in antigen-antibody reactions, for example, in therapeutic drug monitoring or for drugs of abuse determination.

2. Description

Latex agglutination reactions are very popular to monitor biochemical substances in biological fluids, such as urine, serum, etc. A large number of pregnancy tests monitoring human chronic gonadotropin (HCG) in urine is available, which employ this agglutination principle. In a simplified manner, the agglutination inhibition reaction can be thought of as a four step process. (1) Free antigen (Ag) from a subject is added to an antibody (Ab) reagent to form complexes. (2) Latex-bonded antigen (L-Ag) is then added to the complexes and allowed to compete to form other complexes with any unreacted antibody (Ab). (3) As the formation of latex-bonded antigen-antibody complexes continues, aggregation begins to take place. In this phase of the reaction, light transmitted through the sample decreases. (4) As the reaction goes to completion, sometimes taking as long as 90 minutes, the agglutination causes clumping of the sample so that there is a dramatic change in the way the sample looks. Furthermore, after this time period the upper portion of the sample appears clear as aggregates fall to the bottom of the reaction container. During this last step, the light transmitted through the clear upper portion of the reaction container begins to increase. Thus, the reaction can be monitored by visually noting the formation or absence of aggregates (floccules). This is the basis of the prior art non-instrumental or manual agglutination testing.

In the prior art, it also was possible automatically to monitor agglutination reactions using either nephelometry or spectrophotometry. Should analytical methodology such as nephelometry or spectrometry be employed, it is possible to determine the course of the reaction quantitatively in less time and to assign a concentration value to the electronic signal generated from the sample and measured at a given time.

With nephelometry, the light scattered by a sample is obtained by measuring with a detector the scattered power at an angle to the incident light beam. By light scattering, it is meant that small particles interact with incident light and reflect secondary light. The intensity of the scattered light is a function of the relative refractive index, the size parameters and the angle of observation relative to the incident beam. Other sample parameters such as shape, absorption, the concentration and size distribution of the particles and optical anisotropism (i.e., intensity of scattered light as a function of the angle of observation) also influence the intensity distribution of scattered light.

Two competing processes occur during the early course of the latex agglutination reaction using nephelometric technigues. These processes effect the course of what happens to the light directed into the sample which is normally contained in solution. As the particles become larger, the direct transmission of light through the sample, at a small acceptance angle, is reduced. This is due to the increase in the size of the particles due to agglutination. However, as the size of the particles increase, there is an increase in the light which is scattered at small forward angles from the light source.

Once the incident light has interacted with the sample, the scattered light is then detected by the instrument. Different detectors have different spectral response characteristics.

Many different types of light sources are used in prior art nephelometers. The monochromatic, collimated laser beam has high radiant energy density which makes it suitable for scattered light measurements in a forward direction.

The prior art manual and automatic agglutination measuring devices suffer from the disadvantages of requiring significant time to conduct the readings and of being able to read only one sample at a time. Moreover, the insensitivity of the systems to small concentrations in small volumes of samples leads to inaccurate readings reducing their applicability to qualitative rather than quantitative uses.

SUMMARY OF THE INVENTION

The present invention relates to a light-scattering instrument for use in simultaneously measuring multiple antigen-antibody (Ag-Ab) agglutination reactions involving latex particles.

There is described a unique instrument system employing a laser, having a polarized and collimated beam of radiation, which is split into a multitude of primary and secondary beams containing the same desirable properties of high collimation and monochromaticity. Advantageously, the secondary beams are used to measure the agglutination reactions. This system is ideally suited to measuring agglutination reactions and particularly those based on using microparticle latex. Since the laser beam is small, minimal amounts of sample and reagent are required for the measurement.

In accordance with a first embodiment of the invention, a polarized beam from the laser is divided by a beam splitter into a primary signal passing through the beam splitter and a secondary reflective signal reflecting from the beam splitter. The secondary signal passes through a cuvette holding a sample-reagent mixture, and then to a photodetector which produces a signal to quantify an agglutination reaction occurring within the cuvette. The primary signal passing through the beam splitter is passed through a second beam splitter thus producing a second primary signal and a second reflective secondary signal, the latter being passed through a second cuvette with a sample-reagent mixture and to a second photodetector. The primary signal emitted from the second beam splitter is in turn, further split by a preselected number of additional beam splitters into additional primary and secondary beams, and the resulting secondary reflective signals respectively are passed through cuvettes with sample-reagent mixtures and to photodetectors which produce signals that quantify the agglutination reactions. The final primary signal eminating from the last beam splitter then is passed through a polarizer or a graded neutral density filter to adjust signal intensity, and then onto a reference photodetector.

The signals from the various photodetectors and reference photodetector are processed electronically to generate an output of relative transmission versus time for the reactions. This constitutes a quantative measurement of concentration within the samples.

In a second embodiment the prior embodiment is modified such that, the reference beam and its photodetector are eliminated, and the photodetectors respectively receiving the secondary beams are replaced with dual concentric photodetectors respectively positioned in the path of the secondary beams. These modifications eliminate the need for a separate reference circuitry and increase the sensitivity of the system to measure concentrations in the sample-reagent mixtures.

The present invention, thus, provides a simple and accurate technique for simultaneously and quantitatively measuring for therapeutic drug monitoring or for determination of abuse in various biological samples such as serum or urine.

BRIEF DESCRIPTION OF THE DRAWINGS

Preferred embodiments of the invention are described hereinbelow with reference to the drawings wherein:

FIG. 2 is an optical diagram of a second embodiment of the inventive system using concentric dual photodetectors;

FIG. 3 is a diagram of a concentric dual photodetector of FIG. 2;

DETAILED DESCRIPTION OF THE PREFERRED EMBODIMENTS

Figure 1:
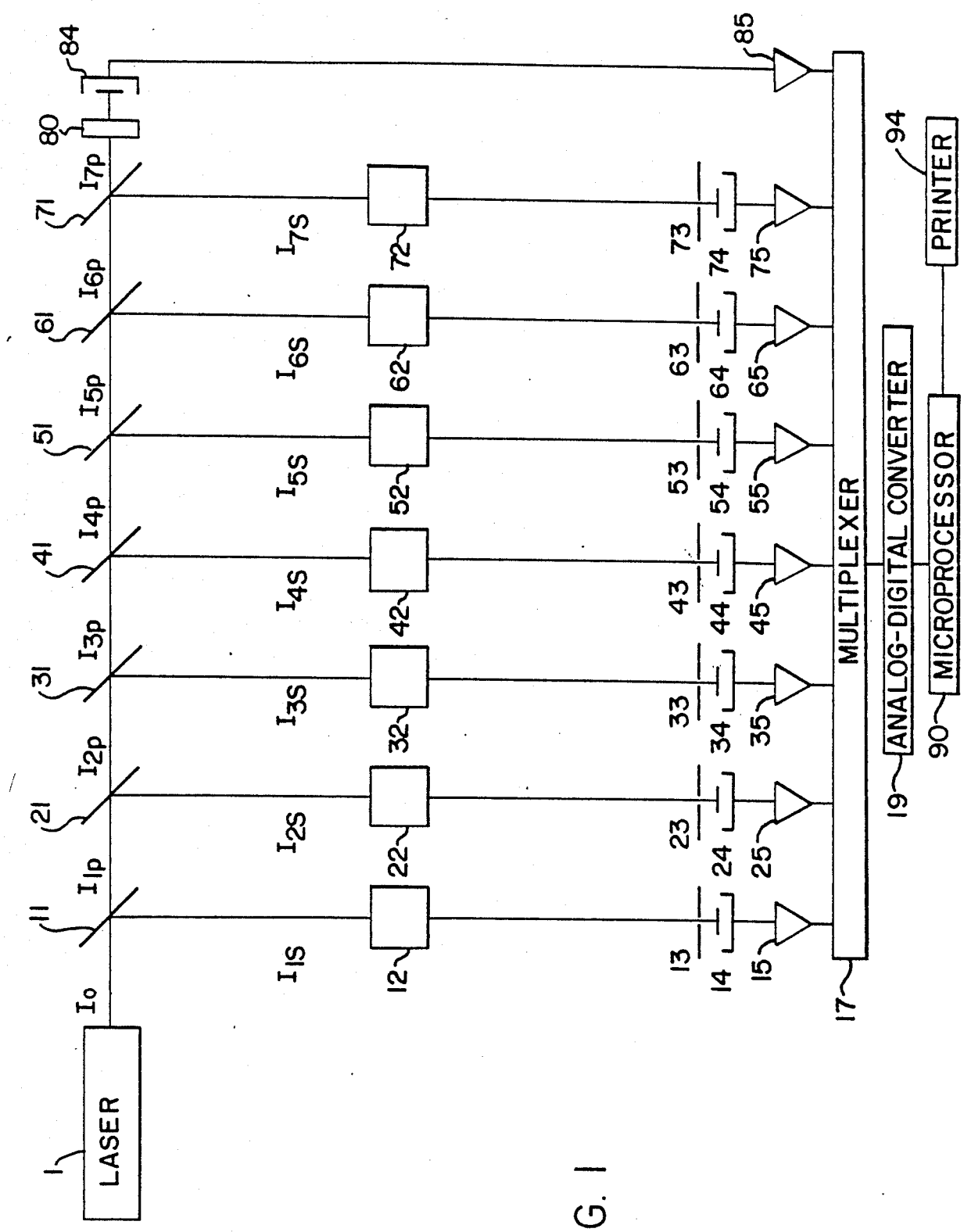
FIG. 1 is an optical diagram of a first embodiment of the inventive instrument system.

The present invention concerns an instrumentation system for the simultaneous measurement of antigen-antibody latex agglutination reactions of sample-reagent mixtures contained in sample containers such as cuvettes.

In accordance with a preferred embodiment of the invention a laser beam is used for generating a beam of monochromatic, polarized, collimated light. A helium-neon, polarized laser is generally used at the wavelength of 632.8 nanometers. The system includes at least two beam splitter means, the first beam splitter means located along the path of the laser beam for dividing the beam into a first primary beam which passes through the first beam splitter means and a first reflective beam which reflects from the first beam splitter means and passes through the first cuvette holding the first sample-reagent mixture. The latex-based immunochemistry products are placed in liquid solution in the sample cuvettes for analysis. The second beam splitter means is located in the path of the first primary beam for dividing the first primary beam into a secondary beam which passes through the second beam splitter means and a second reflective beam which reflects from the second beam splitter means and passes through the second cuvette holding the second sample-reagent mixture.

The system also includes first aperture means positioned in the path of the first reflective beam passing through the first cuvette, and second aperture means positioned in the path of the second reflective beam passing from the second cuvette for restricting the amount of the beam respectively passing therethrough. A first photodetector is positioned after the first apparatus means in the path of the first reflective beam and a second photodetector is positioned after the second apparatus means in the path of the second reflective beam. The system also includes a reference photodetector located in the path of the primary beam passing through the last beam splitter (i.e., the second beam splitter means in the case of a two beam splitter means system) to act as a reference. The system also includes electronic means for processing the output from the at least first, second and reference photodetectors and microprocessing means for analyzing the outputs from the processing means and obtaining a read-out of transmission versus time for each sample-reagent mixture.

In another embodiment of the present invention there is disclosed a system having at least two beam splitter means, the first beam splitter means located along the path of the laser beam for dividing the beam into a first primary beam which passes through the first beam splitter means and a first reflective beam which reflects from the first beam splitter means and passes through the first cuvette holding the first sample-reagent mixture. The second beam splitter means is located in the path of the first primary beam for dividing the first primary beam into a second primary beam which passes through the second beam splitter means and a second reflective beam which reflects from the second beam splitter means and passes through the second cuvette with the second sample-reagent mixture.

The system also includes a first photodetector means which is positioned in the path of the first reflective beam passing from the first cuvette. The first photodetector means has two photodetector segments—a central segment and a peripheral segment surrounding the central segment but electrically isolated from each other by means of an insulating mask. The system also includes at least a second photodetector means positioned in the path of the second reflected beam passing from the second cuvette. The second photodetector means has two photodetective segments—a central segment and a peripheral segment which are isolated from each other by an insulating mask. In an especially preferred embodiment, these photodetector means have a circular central segment surrounded by a donut shaped or toroidal, concentric mask which in turn is surrounded by a donut shaped or toroidal, concentric peripheral segment.

The system also includes means for electrically processing the output from the at least first and second photodetector means, and microprocessing means for analyzing the output from the processing means to obtain a plot of signal ratio from each photodetective segment versus time for each sample-reagent mixture.

FIG. 1 is an optical diagram of a seven channel system for simultaneously measuring seven samples. The figure shows a laser 1; seven beam splitters 11, 21, 31, 41, 51, 61, and 71; seven cuvettes 12, 22, 32, 42, 52, 62, and 72; seven apertures 13, 23, 33, 43, 53, 63, and 73; seven photodetectors 14, 24, 34, 44, 54, 64, and 74; seven operational amplifiers 15, 25, 35, 45, 55, 65, and 75; a signal multiplexer 17 with eight inputs and one output; an analog-to-digital converter 19; a polarizer or graded neutral density filter 80, a reference photodetector 84; a reference operational amplifier 85; a microprocessor 90; and a digital readout printer 94.

The polarized laser beam $I_o$ is set in such a direction as to undergo favorable reflection at each of the beam splitter interfaces. A helium-neon laser is generally used at the wavelength of 632.8 nanometers. Randomly polarized lasers preferably should not be used because the reflected energy at the beam splitters will change as the polarization changes, resulting in a non-constant measuring beam and potentially inaccurate readings.

In the embodiment of FIG. 1, the collimated laser incident beam $I_o$ is split into two beams (a primary beam $I_{1p}$ and a secondary beam $I_{1s}$ using a thin glass plate) as beam splitter 11 set at approximately a 45-degree angle to the incident beam $I_o$. The seven beam splitters can be positioned at other than 45° angles from the incident beam. For example, they may be individually positioned to take into consideration the location of samples along a curved path. It, however, is preferred that all the beam splitters be set at the same angle and that being 45°. Of course, the various beam splitters should not be set so that their secondary beams reflecting from the beam splitters intersect more than one sample (e.g., not intersect other samples in other cuvettes of the systems).

Since the index of refraction of glass (of the beam splitter) is different from that of air, there is about a four percent reflection at each air-glass interface of beam splitter 11. This results in approximately eight percent (front and rear glass surfaces) of the intensity being split off at right angles to the incident beam thus forming secondary beam $I_{1s}$. The reflection at one of the air-glass surfaces may be reduced by using an anti-reflection coating for the laser wavelength which is chosen. These coatings are conventionally available depending upon the wavelength selected for the laser. The coating would reduce the fraction of light reflected at each beam splitter.

The beam splitters of the inventive systems include conventional devices for splitting light into two beams, such as glass plates, non-vibrational pellicles, prisms and the like, preferably, conventional microscope cover glasses and devices of similar dimensions are employed. The glass plates should be as thin as possible to minimized parallax but preferably not so thin as to vibrate from external noise and movement.

The signal (i.e., $I_{1p}$) passing through beam splitter 11 then passes through beam splitter 21 and at this point again is split into two beams (a primary beam $I_{2p}$ and a secondary beam $I_{2s}$) by beam splitter 21 set at approximately a 45° angle to incident beam $I_{1p}$. Without the anti-reflection coating, as with beam splitter 11, approximately 8% of the intensity of beam $I_{1p}$ is reflected at 90° from the incident beam $I_{1p}$ (45° angle into beam splitter 21 and 45° out) thus forming secondary beam $I_{2s}$. Should the anti-reflection coating be utilized at one air-glass interface, approximately 4% of the intensity of beam $I_{1p}$ is reflected from beam splitter 21 thus allowing 96% of the energy in beam $I_{1p}$ to remain in the primary beam and pass through beam splitter 21 on to beam splitter 31.

Similarly primary beams $I_{3p}$, $I_{4p}$, $I_{5p}$, $I_{6p}$, and $I_{7p}$ and secondary reflective beams $I_{3s}$, $I_{4s}$, $I_{5s}$, $I_{6s}$, and $I_{7s}$ respectively are formed from light passing through or reflecting from beam splitters 31, 41, 51, 61, and 71.

These secondary beams $I_{1s}$–$I_{7s}$ retain the desirable properties of being monochromatic and collimated (spatial coherence). The secondary beams $I_{1s}$–$I_{7s}$ respectively are directed through cuvettes 12–72, which contain the sample-reagent mixtures and which are transparent to the wavelength of radiation used for the tests. Since reaction rates are dependent on temperature, advantageously, the cuvettes are maintained at a predetermined constant temperature, preferably about 22° C. to about 37° C., by a heat block (not shown).

Apertures 13–73 are used to limit the acceptance angle of the beams exiting the cuvettes and passing to photodetectors 14–74 respectively. In FIG. 1, the beam which passes through the respective aperture, thus, is limited in angle by the size of the aperature and by the distance between the aperture and the photodector. It optionally can pass through an interference filter (not shown) to reduce the background from any stray room light before passing to the photodector. The limitation in acceptance angle must be selected such that it preferably is less than approximately twenty-five milliradians, preferably 5–15 milliradians, to avoid the disadvantage of having too high of an intensity of forward scattering (too wide an acceptance angle of the laser light). Any conventional spectrophotometer or aperture can be utilized provided it achieves the above described acceptance angle. The acceptance angle in radians is defined as the ratio of the photodetector diameter to the distance between the photodetector and the scattering center of the sample.

If very small diameter (e.g., approximately less than 25 milliradian acceptance angle) photodiodes 14–74 are used and positioned to intercept the central portion of the secondary beam exiting from the sample, an aperture (e.g. as shown in FIG. 1) is not necessary because the central portion of the beam having a radius beyond that of the preselected central photodetector is not measured or utilized.

Photodiode detectors 14–74 (e.g., conventional silicon type) are sensitive to the radiation from the laser. Any conventional photodetector can be utilized and would be known to a skilled artisan.

The outputs from photodiodes 14–74 are directed into conventional operational amplifiers 15–75 used as current-to-voltage converters where the signal is amplified. The outputs from the operational amplifiers are directed to multiplexer 17 which switches sequentially between the various outputs from the operational amplifiers to the input of the analog-to-digital converter 19.

Once a signal is digitized by the analog-to-digital converter 19, it is fed into microprocessor 90. This component stores this information, computes the algorithms and stores the final information for subsequent data plotting by digital read-out by printer 94. By ratioing in the microprocessor each initial intensity to reference intensity in the microprocessor relative transmission or transmittance can be obtained for each sample as a function of time. The operation amplifiers, multiplexers, analog-to-digital converter and microprocessor are conventional and within the skill of an artisan to select and interconnect.

Additionally, the system can have hard-copy capability of read-out by printer 94 allowing the sample to be identified and a permanent record to be kept to preserve the chain-of-custody of the sample and an objective, readily retrievable record.

If the progress of the original polarized beam $I_o$ from laser 1 is followed through the beam splitters, it can be seen that the intensity of the primary signals $I_{1p}$–$I_{7p}$ continues to decrease as approximately eight percent of the energy at each step is removed to the secondary beam, while 92 percent of the intensity at that step remains in the primary beam. Should an anti-reflection coating be utilized then 96 percent remains in the primary beam. The ultimate beam $I_{7p}$ is then adjusted by orienting polarizer 80 to reduce its intensity such that it can be utilized by reference photodiode 84. Obtaining appropriate intensity via polarizer 80 is within the skill of an artisan.

The same type of photodiode detector can be used for photodetector 84 as for photodetector 14–74, photodetector 84 is employed to detect the final intensity $I_{7p}$ of the original beam $I_o$. The signal generated from $I_{7p}$ is processed by the reference circuitry including operational amplifier 85, multiplexer 17, analog-to-digital converter 19 and microprocessor 90 in the same way as the signals from the seven channels are processed. As discussed below, the reference circuitry and the algorithm employed allows compensation for variations of the laser signal intensity during the measurement period. This is usually in the order of three to five percent after an initial warm-up period of approximately five minutes. The circuitry used for the reference channel is conventional and would be within the skilled of an artisan to obtain. See e.g. M. Franklin "Instrumentation In Clinical Chemistry", Clinical Biochemistry, Contemporary Theories and Techniques, Volume 3 (Academic press, Inc. 1984), pages 154–169, and U.S. Pat. No. 4,241,998 which publications are incorporated herein by reference.

In accordance with the invention, experimental curves taken as a function of time show the transmittance signal initially to decrease monotomically as a result of sample-reagent agglutination. The equation which describes the output signal intensity for channel i at time $t_o + n\Delta t$ is:

$$\text{Signal}_i = \frac{I_i(t_o + n\Delta t) \cdot I_{REF}(t_o)}{I_i(t_o) \cdot I_{REF}(t_o + n\Delta t)}$$

where "$I_i$" is intensity of channel i or the reference, "i" is the channel number (i.e., 1 to 7 for a seven channel system), $I_{REF}$ is the intensity of the reference channel, "$t_o$" is the starting time of the reaction, and "$\Delta t$" is the time between successive measurements of the reaction.

By utilizing reference circuitry in the system to implement this equation, the initial condition of the sample is normalized so that all relative transmission measurements are taken with that as an initial starting point. In accordance with this application, relative transmission of channel i is defined as the ratio of the intensity of the light passing through the sample "i" to the intensity of the reference light ($I_{7p}$) at any given time. ($I_i(t_o+n\Delta t)/I_i(t_o)$ = relative transmission). Percent transmission is the transmittance multiplied by 100 (i.e. one converts transmittance into a percentage). Thus, small changes in attenuation of the beam due to scratches or particles on the sides of the cuvette are compensated, and thus precision of the measurement is increased. By use of this equation, one also divides the channel signal by the reference signal during each moment of testing, which allows compensation for changes in the intensity of the laser during the period of the sample measurement. Reference or standard curves can be plotted and compared (manually or automatically) against the relative transmission values obtained for the samples to determine concentration values.

The embodiment of FIG. 1 is used with latex based immunochemistry reagents illustratively for the analysis for seven different drugs of abuse. Any conventional latex based immunochemical reagents can be employed, many of which are commercially available.

The illustrated system is operated with seven different measurement channels plus a reference channel. Other numbers of measurement channels, of course, are contemplated and within the skill of an artisan.

The laser intensity is sufficient to provide many measurement channels plus a reference channel. Without the anti-reflective coating, the intensity of any secondary beam(s) is given by the formula:

$$I_{is} = I_{1s}(0.92)^{i-1}$$

wherein i is the channel and $I_{1s}$ is the intensity of the secondary beam of channel 1.

For example, without the anti-reflection coating the seventh secondary beam ($I_{7s}$) has 61 percent of the intensity of the first secondary beam ($I_{1s}$).

The sub-micron particle size latex does not need mechanical stirring after an initial mixing since the latex particles are small enough in size to be driven by Brownian motion. This, in effect, provides mixing of the reagents without the problems caused by mechanical stirring (e.g., entrainment of bubbles which can cause noise in the measured signal). Noise is defined to be any fluctuation in the signal not due to the sample reaction itself.

The second embodiment of the invention as described in FIGS. 2 and 3 employs for each channel concentric photodiode detectors 14d–74d of specialized geometry which act as replacements for the seven apparatus and all the photodiode detectors of the embodiment of FIG. 1. The photodectors 14d–74d have three segments-central segment 91, outer segments 92 and isolating segment 93. Photodetector segment 91, centered along the axis of the beams, measures the narrow beam transmission through the sample during the course of the reaction. This transmission detected by photodetector 91 decreases in magnitude during the first minutes of the reaction similar to that indicated by FIG. 5.

Preferably the diameter of photodetector segment 91 is positioned and/or selected such that the beam has approximately less than a 25 milliradian acceptance angle. With respect to the embodiment of FIG. 2, there is no need to utilize an aperture and, thus, one is not shown. One can select a dual concentric diode with dimensions for inner segment 91 to achieve an acceptance angle of approximately less than 25 milliradians. Round, washer-shaped mask 93 is employed to isolate electronically and optically some of the ambiguous signals around the perimeter of small photodiode 91, and larger washer-shaped diode 92 is placed concentrically along the axis of the beam about central portion 91 to detect the cone of forward scattered radiation for the secondary beam. Two signals thus, are detected by each of photodetectors 14d–74d during the course of the reactions, in which one (outside) increases in magnitude while the other (inside) decreases in magnitude.

In accordance with the invention, these signals from photodetector segments 91 and 92 are ratioed in such a way that the forward scattered intensity (signal from photodetector segment 92) is divided by the transmitted intensity (signal from photodetector segment 91). An increase in sensitivity of the measurement over that obtained by the embodiment of FIG. 1 thus is made by utilizing this ratio technique. This has the effect of changing the slopes of the resulting line plot so that the curves presented, for example, in FIG. 5 would have more separation between them for various concentrations. This results in higher sensitivity or more certainty of the measurement at a particular value. The need for certainty is often important for measurement of specimens for drugs of abuse.

In the embodiment of FIGS. 2 and 3, use of both the forward angle scattering beam and the transmitted beam eliminates the need for the reference detector signal. The equation describing the output signal intensity for channel i at time $t_o+n\Delta t$ is:

$$Signal_i = \frac{I_i(t_0 + n\Delta t)/I_i(t_0)}{I^{fs}_i(t_0 + n\Delta t)/I^{fs}_i(t_0)}$$

where $I^{fs}_i$ is the intensity of the forward scattering for channel i.

By using the ratio of the forward scattering intensity divided by the transmitted intensity, there is eliminated the need for a signal from separate reference detector components such as polarizer 84 and reference photodiode 85 of FIG. 1 and its reference signal processing circuitry (e.g., operation amplifier 85) to compensate for any intensity changes in laser 1 during the measurement time. This provides stability and precision in the measurement. A more sensitive measure of the course of the latex agglutination reaction, thus, is produced. Since, however, the reference circuitry of FIG. 1 has been eliminated there is required additional operational amplifiers 16, 26, 36, 46, 56, 66, and 76 which are utilized for the outer portion 92 of the photodiode. All operational amplifiers 15-75 and 16-76 are then inputed into multiplexer 17 which in turn is fed into analog-to-digital converter 19 which in turn is processed by microprocessor 90. If desired a digital read-out can be provided by digital read-out 94.

Figure 4:
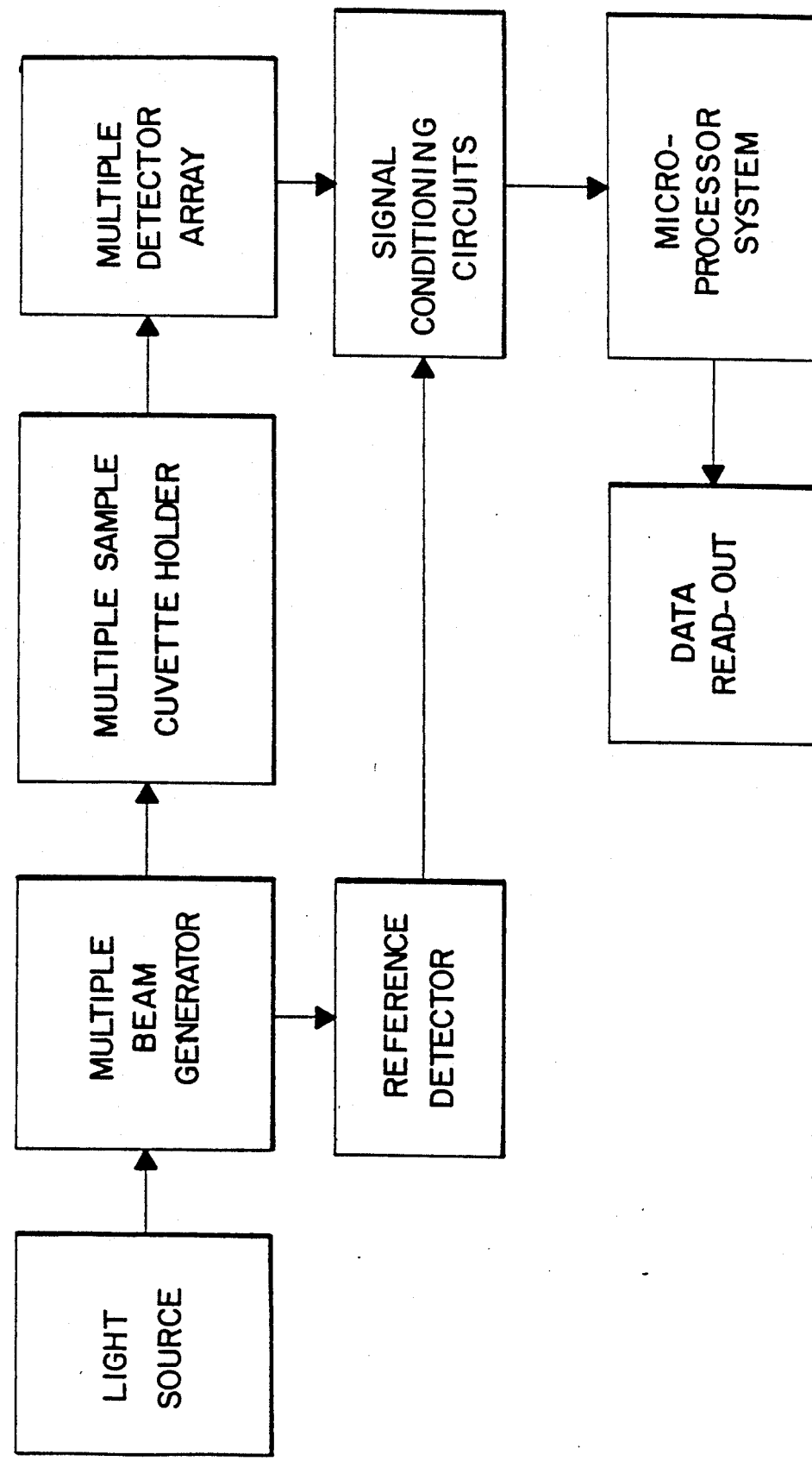
FIG. 4 is a block diagram of the inventive system of FIGS. 1–3.

FIG. 4 is a block diagram of the inventive latex agglutination system described with reference to FIGS. 1-3. In FIG. 4, there is shown a Light Source which corresponds to laser 1 of FIGS. 1-2. Multiple Beam Generator corresponds to beam splitters 11-71 of FIGS. 1-2 which generate primary beams $I_{1p}$–$I_{7p}$ and secondary beams $I_{1s}$–$I_{7s}$. Multiple Sample Cuvette Holder corresponds to cuvettes 12-72. Multiple Detector Array corresponds to apertures 13-73, photodiodes 14-74 of FIG. 1 and segments 91 of photodiodes 14d-74d of FIGS. 2-3. Signal Conditioning Circuits correspond to operational amplifiers 15-85, multiplexers 17 and analog-digital converter 19 of FIG. 1 and operational amplifiers 15-75 and 16-76, multiplexer 17 and analog-digital converter 19 of FIG. 2. Microprocessor System corresponds to microprocessor 90 of FIGS. 1 and 2. Data Read-Out corresponds to printer 94 of FIGS. 1 and 2. Reference Detector corresponds to photodiode 84 of FIG. 1 and segments 92 of photodiodes 14d-74d.

The operation of the inventive system as setforth in the block diagram of FIG. 4 is described above in detail with reference to FIGS. 1-3.

The following non-limiting example illustrates the invention and its uses. Unless otherwise included the example was carried out as written.

EXAMPLE

The methods for measuring drugs of abuse in urine (DAU) are based upon a latex agglutination-inhibition reaction employing a latex bound antigen. These tests are sensitive homogeneous immunoassays requiring only two reagents. The components consist of an antigen bonded to latex polymer particles and an anti-serum containing antibodies to the analyte. When the antiserum is mixed with the latex-antigen reagent, a complex is formed that results in an increase of the turbidity of the solution. In the absence of free antigen (the drug to be measured), maximum turbidity will result. Thus, when the antiserum is mixed with an urine specimen containing a detectable amount of antigen, some of the antibodies will be complexed, so that they will no longer be available to react with latex-antigen. A decrease in turbidity and absorbance or an increase in transmittance will result. With the use of standards, cut-off values are developed to determine whether or not a urine sample contains significant concentrations of a drug.

The following reagents were utilized for the tests and are produced by known immunochemistry and organic chemistry technologies. These reagents are similar in nature to the reagents utilized in the PETINA (particle enhanced turbidimetric inhibition immunoassay) latex agglutination tests of DuPont. See e.g., Clin. Chem. 30, 1489-1493 (1984).

| Analyte | Dilution of Antiserum (AS)Reagent (Antibody) | Latex Reagent (Antigen) |
| --- | --- | --- |
| 1. Morphine | 1:88 MES buffer with 1% normal rabbit serum | 2 mg/ml TRIS-saline buffer |
| 2. Amphetamine | 1:260 TRIS-saline-0.37% EDTA | 1.7 mg/ml glycine buffer |
| 3. PCP | 1:150 TRIS-saline-0.37% EDTA | 2 mg/ml glycine buffer |
| 4. Benzodiazepine | 1:100 Phosphate buffer pH 6.7 | 4 mg/ml TRIS-saline |
| 5. Barbiturate | 1:100 MES buffer pH 6.5 | 2 mg/ml MES buffer |
| 6. Cocaine | 1:30 TRIS-saline-0.37% EDTA | 4 mg/ml glycine buffer |
| 7. THC | 1:25 MES buffer with 0.01% PEG | 2 mg/ml glycine buffer |

The parameters were as follows:

| Analyte | Sample Volume | AS Reagent Volume | Latex Volume | Measurement Time |
| --- | --- | --- | --- | --- |
| 1. Morphine | 0.2 ml | 2.5 ml | 0.3 ml | 5 min. |
| 2. Amphetamine | 0.2 ml | 2.0 ml | 0.4 ml | 5 min. |
| 3. PCP | 0.3 ml | 2.0 ml | 0.2 ml | 5 min. |
| 4. Benzodiazepine | 0.2 ml | 2.0 ml | 0.2 ml | 5 min. |
| 5. Barbiturate | 0.2 ml | 2.0 ml | 0.3 ml | 5 min. |
| 6. Cocaine | 0.2 ml | 2.0 ml | 0.2 ml | 5 min. |
| 7. THC | 0.2 ml | 2.0 ml | 0.3 ml | 5 min. |

In the above tables, the abbreviations have the following meanings:
PCP=phencyclidine THC=tetrahydrocannabinol
MES=2-[N-morpholino]ethansulfonic acid
TRIS=Tris(Hydroxymethyl)aminomethane hydrochloride
EDTA=ethylenediaminetetraacetic acid
PEG=polyethylene glycol The procedure consisted as follows:
1. Pipet the indicated antiserum reagent and its volume into an appropriately labeled cuvette.
2. Add 0.2 ml urine sample (0.3 ml for PCP only) to each cuvette and mix.
3. Add the indicated latex reagent and its volume into the appropriate cuvette. Cap and mix all cuvettes.
4. Place cuvettes into reader.
5. Initialize reader with appropriate keyboard entries.
6. Press the start button.
7. Use keyboard entries to obtain printout.

The inventive multi-channel system with the supporting chemical test systems allowed the simultaneous measurement of these above 7 drugs of abuse in a total time of 10 minutes. Although the actual measurement time of the reaction was 5 minutes, an additional 5 minutes was required for technical manipulations.

A relative transmittance of 60% was selected as the cut-off point for all analytes. All channels were calibrated to indicate a positive result at the cut-off value or the corresponding analyte concentration. Since the transmittance value at the cut-off was identical for all channels, this allowed the possibility of running 7 of the same test for different urine samples.

RESULTS

Figure 5:
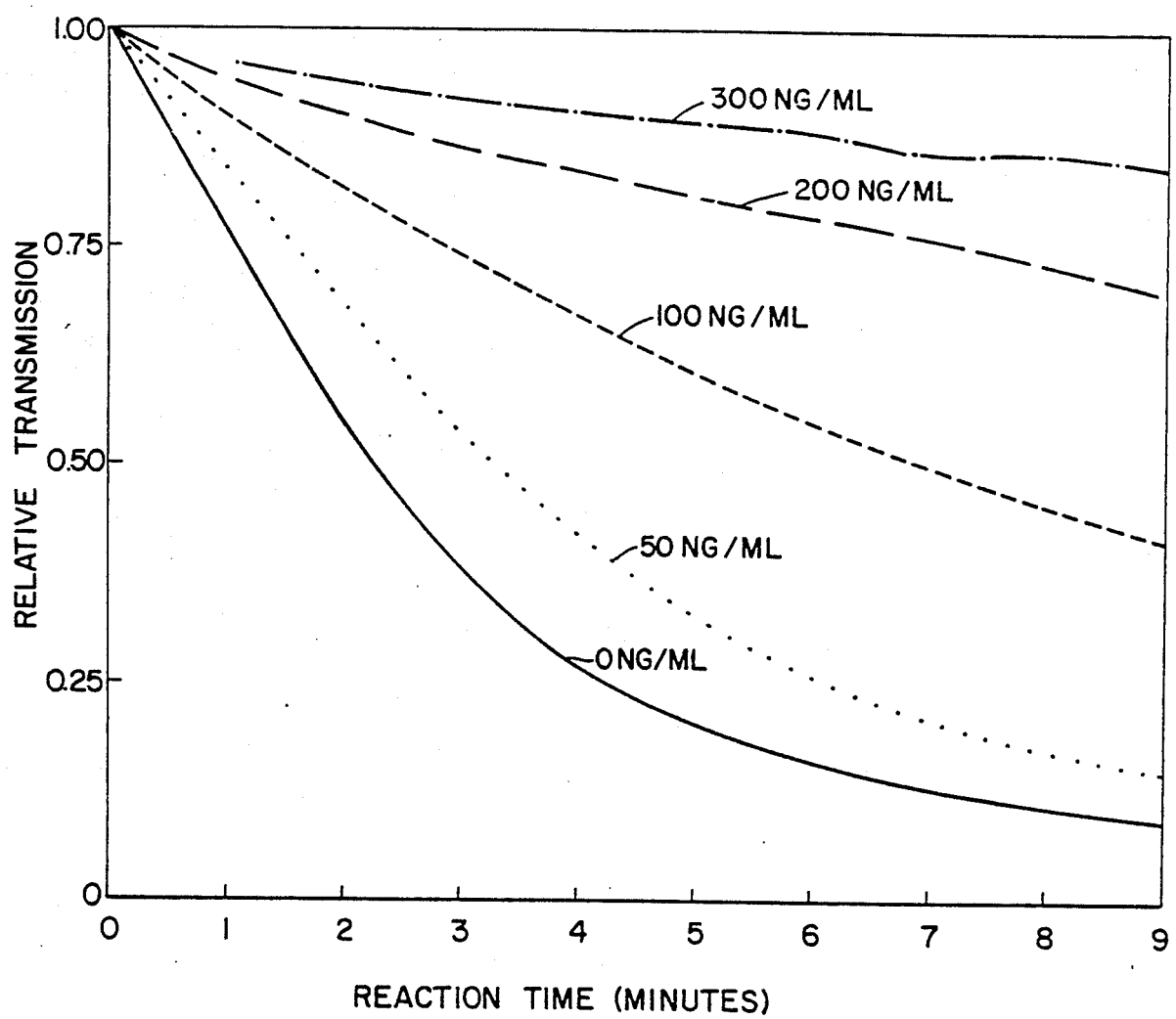
FIG. 5 is a graph of transmission versus time of 0–300 nanograms per milliter (ng/ml) concentrations of cocaine in samples as detected by the inventive system of FIG. 1.

Experimental data for the analysis of cocaine in urine sample 6, are presented in FIG. 5. The cocaine reaction was quantified using the inventive instrumentation system in five to ten minutes. As seen from FIG. 5, the relative transmission value (which is a measure of concentration of drug being tested) continually decreases with reaction time. Each curve showed the transmittance values for separate cuvettes which have differing relative transmission values at given times when the concentration of substance was varied. This plot was found to be reproducible. Accordingly, one could use the graph to conclude that should a sample containing cocaine generate a reading of 0.5 after 3.3 minutes, then the sample would have a concentration of approximately 50 ng/ml cocaine.

While the invention has been described in conjunction with certain embodiments, it is understood that various modifications and changes may be made without departing from the spirit and scope of the invention.

As is obvious from this specification although seven samples and seven channels where utilized in the embodiments, it is possible and within the contemplation of the invention to use more or less samples and thus more or less channels within the scope of the invention. For example, should one obtain a conventionally available sixteen channel multiplexer one might wish to utilize a system which could analyze up to fifteen samples simultaneously and thus have fifteen channels for use and one reference channel. In accordance with the invention, it is preferred to utilize as many as possible channels to permit simultaneous reading of many samples and thus take advantage of the invention as described within this application.

As another example, reference photodetector 84 of FIG. 1 can be located in the path of a secondary beam (e.g. $I_{7s}$) provided that the selected secondary beam does not pass through a sample. With this arrangement, there would be no need to utilize polarizer 80 to adjust the intensity of the reference beam.

We claim:

1. A method for measuring antigen-antibody reactions in a plurality of samples containing latex bonded antigen-antibody complexes by utilizing a multi-channel system having a laser for generating a beam of polarized, collimated light, and at least two beam splitters, the first beam splitter located int he path of the laser beam and positioned to divide the beam into a first primary beam which passes through the first beam splitter and a first reflective beam which reflects from the first beam splitter, the second beam splitter located in the path of the first primary beam passing through the first beam splitter and dividing this beam into a second primary beam passing through the second beam splitter and a second reflective beam reflecting from the second beam splitter, at least first and second samples being respectively located in the paths of the reflective beams, at least first and second detecting means each having a central detecting segment for detecting the transmission intensity of forward scattered light from the reflective beams which respectively pass through the at least first and second samples; reference detecting means located in the path of the last primary beam or in the path of a reflective beam not having a sample passing therethrough for detecting the transmission intensity of a reference beam; processing means operatively communicating with the detecting means for converting the transmission intensities into digitized electrical signals; and a microprocessor means operatively communicating with the processing means for analyzing the signals from the processing means and evaluating the transmission intensity of each sample relative to the transmission intensity of the reference beam as a function of time, the method comprising:

(a) passing a polarized, collimated laser beam through said beam splitters;

(b) positioning said at least first and second samples in the path of the reflective beams respectively;

(c) positioning said at least first and second detecting means such that their central segments are in the path of the reflective beams respectively exiting said at least first and second samples, and selecting said detecting means so as to achieve an acceptance angle of less than approximately 25 milliradians relative to the path of the respective reflective beam prior to its passing through the respective at least first and second samples;

(d) detecting the transmission intensity of forward scattered light of the respective reflective beams caused by passing said reflective beams through said at least first and second samples by means of the respective central segment of said at least first and second detecting means;

(e) detecting the transmission intensity of the reference beam by means of the reference detecting means;

(f) converting the transmission intensities of said reflective beams and reference beam into respective individual digitized electrical signals by means of the processing means; and (g) evaluating said digitized electrical signals by means of the microprocessor means according to the formula:

$$\frac{I_i(t_0 + n\Delta t) \cdot I_{REF}(t_0)}{I_i(t_0) \cdot I_{REF}(t_0 + n\Delta t)}$$

wherein $I_i$ is the transmission intensity of the forward scattered light of the $i^{th}$ reflective beam as detected by the $i^{th}$ detecting means, i is an integer from 1 (first) to at least 2 (second) representing the $i^{th}$ sample, $I_{REF}$ is the transmission intensity of the reference beam detected by said reference detecting means, $t_O$ is the starting time of the respective antigen-antibody reaction, n is an integer from 0 to infinity, and $\Delta t$, is the time between successive measurements of the respective reaction, thereby providing a measure of the antigen-antibody reaction of each sample as a function of time.

2. A method for measuring antigen-antibody reactions in a plurality of samples containing latex bonded antigen-antibody complexes by utilizing a multi-channel system having a laser for generating a beam of polarized, collimated light, and at least two beam splitters, the first beam splitter located int he path of the laser beam and positioned to divide the beam into a first primary beam which passes through the first beam splitter and a first reflective beam which reflects from the first beam splitter, the second beam splitter located in the path of the first primary beam passing through the first beam splitter and dividing this beam into a second primary beam passing through the second beam splitter and a second reflective beam reflecting from the second beam splitter, at least first and second samples being respectively located int he paths of the reflective beams, at least first and second detecting means each having a central detecting segment for detecting the transmission intensity of forward scattered light from the reflective beams which respectively pass through the at least first and second samples, and each detecting means having a peripheral photodetecting segment substantially surrounding but electronically and optically isolated from its central segment so as to receive the transmission intensity of the forward scattered light from the reflective beam intercepted by such peripheral segment; processing means operatively communicating with the detecting means for converting the transmission intensities into digitized electrical signals; and a microprocessor means operatively communicating with the processing means for analyzing the signals from the processing means and evaluating the transmission intensity of each sample intercepted by the central segment of the respective detecting means relative to such transmission intensity intercepted by the peripheral segment of the same detecting means as a function of time, the method comprising:

(a) passing a polarized, collimated laser beam through said beam splitter;
(b) positioning said at least first and second samples in the path of the reflective beams respectively;
(c) positioning said at least first and second detecting means such that their central segments are in the path of the reflective beams respectively exiting said at least first and second samples, and selecting the detecting means so as to achieve with its central segment an acceptance angle of less than approximately 25 milliradians relative to the path of the respective reflective beam prior to its passing through the respective at least first and second samples;
(d) detecting the transmission intensity of forward scattered light of the respective reflective beams caused by passing said reflective beams through said at least first and second samples by means of the respective central segment of said at least first and second detecting means;
(e) detecting the transmission intensity of forward scattered light of the respective reflective beams caused by passing said reflective beams through said at least first and second samples by means of the respective peripheral segment of the detecting means;
(f) converting the transmission intensities of forward scattered light of said reflective means intercepted by said central and peripheral segments of the detecting means into respective individual digitized electrical signals by means of the processing means; and
(g) evaluating said digitized electrical signals by means of the microprocessor means according to the formula:

$$\frac{I_i(t_0 + n\Delta t)/I_i(t_0)}{I_i^{fs}(t_0 + n\Delta t)/I_i^{fs}(t_0)}$$

wherein $I_i$ is the transmission intensity of the forward scattered light of the $i^{th}$ reflective beam as detected by the central segment of the $i^{th}$ detecting means, i is an integer from 1 (first) to at least 2 (second) and represents the $i^{th}$ sample, $I^{fs}{}_i$ is the transmission intensity of forward scattered light intercepted by the peripheral segment of the $i^{th}$ detecting means of the $i^{th}$ reflective beam, $t_O$ is the starting time of the respective antigen-antibody reaction, n is an integer from 0 to infinity, and at $\Delta t$ is the time between successive measurements of the respective reaction, thereby providing a measure of antigen-antibody reaction of each sample as a function of time.

* * * * *

UNITED STATES PATENT AND TRADEMARK OFFICE
CERTIFICATE OF CORRECTION

PATENT NO. : 4,988,630
DATED : January 29, 1991
INVENTOR(S) : Fang-Chung Chen and Michael L. Franklin It is certified that error appears in the above-identified patent and that said Letters Patent is hereby corrected as shown below:

In claim 1, column 12, line 10, delete "int he" and insert therefor -- in the --.

In claim 2:

Column 13, line 23, delete "int he" and insert therefor -- in the --.

Column 14, line 28, delete "means" and insert therefor -- beams --;

Column 14, line 45, delete "$I^{fs}{}_i$" and insert therefor -- $I^{fs}_i$ --

Column 14, line 50, after "and" and before "$\Delta t$" delete "at".

Signed and Sealed this

Fifteenth Day of December, 1992

Attest:

DOUGLAS B. COMER

Attesting Officer      Acting Commissioner of Patents and Trademarks